(12) United States Patent
Matsumoto

(10) Patent No.: US 11,441,113 B2
(45) Date of Patent: Sep. 13, 2022

(54) CELL TREATMENT SYSTEM

(71) Applicant: KATAOKA CORPORATION, Kyoto (JP)

(72) Inventor: Junichi Matsumoto, Kyoto (JP)

(73) Assignee: KATAOKA CORPORATION, Kyoto (JP)

( * ) Notice: Subject to any disclaimer, the term of this patent is extended or adjusted under 35 U.S.C. 154(b) by 415 days.

(21) Appl. No.: 16/305,378

(22) PCT Filed: Mar. 24, 2017

(86) PCT No.: PCT/JP2017/012059
§ 371 (c)(1),
(2) Date: Nov. 28, 2018

(87) PCT Pub. No.: WO2017/208589
PCT Pub. Date: Dec. 7, 2017

(65) Prior Publication Data
US 2020/0325432 A1    Oct. 15, 2020

(30) Foreign Application Priority Data

Jun. 1, 2016 (JP) .............................. JP2016-110131

(51) Int. Cl.
*C12M 1/42* (2006.01)
*C12M 1/00* (2006.01)
(Continued)

(52) U.S. Cl.
CPC ............ *C12M 35/02* (2013.01); *C12M 23/20* (2013.01); *C12M 23/22* (2013.01); *C12M 41/36* (2013.01); *C12N 13/00* (2013.01)

(58) Field of Classification Search
CPC ........ C12M 1/42; C12M 23/20; C12M 23/22; C12M 35/02; C12M 41/36; C12N 1/00;
(Continued)

(56) References Cited

U.S. PATENT DOCUMENTS 4,629,687 A * 12/1986 Schindler ................ B07C 5/342
435/286.2
6,615,141 B1 * 9/2003 Sabry ................. G06K 9/00127
702/19
(Continued)

FOREIGN PATENT DOCUMENTS

JP    2009-528043 A    8/2009
JP    2009-195110 A    9/2009
(Continued)

OTHER PUBLICATIONS

Kristi A. Hohenstein Elliott,et al., "Laser-Based Propagation of Human iPS and ES Cells Generates Reproducible Cultures with Enhanced Differentiation Potential", Stem Cells International, vol. 2012 (Year: 2012).*

(Continued)

*Primary Examiner* — Holly Kipouros
(74) *Attorney, Agent, or Firm* — Scully, Scott, Murphy & Presser, P.C.

(57) ABSTRACT

A cell treatment system includes an analysis unit to calculate the area or size of each of cell aggregates existing on the cell culture vessel based on an image; a display device to show the area or size of each of the cell aggregates on a display; a laser irradiator to emit laser toward the cell culture vessel so as to kill cells existing on the cell culture vessel; an input device to receive an operation input designating cells to be killed with irradiation of the laser or cells to survive without the irradiation of the laser among the cells existing on the cell culture vessel, or an operation input designating a position to be irradiated with the laser or a position not to be irradiated with the laser on the cell culture vessel; and a control unit to control a position irradiated with the laser.

20 Claims, 7 Drawing Sheets

(51) Int. Cl.
*C12M 1/34* (2006.01)
*C12N 13/00* (2006.01)

(58) Field of Classification Search
CPC ... C12N 5/00; C12N 5/04; C12N 5/07; C12N 13/00
See application file for complete search history.

(56) References Cited

U.S. PATENT DOCUMENTS

| | | | | |
|---|---|---|---|---|
| 2001/0005586 | A1* | 6/2001 | Palsson | C12M 41/46 435/40.5 |
| 2001/0041347 | A1* | 11/2001 | Sammak | G01N 33/5076 435/7.23 |
| 2008/0057558 | A1* | 3/2008 | Niwa | G02B 21/0088 435/173.9 |
| 2011/0189650 | A1* | 8/2011 | Ayliffe | C12M 47/04 435/3 |
| 2013/0023025 | A1* | 1/2013 | Sumaru | C12N 1/02 435/173.9 |
| 2013/0156287 | A1* | 6/2013 | Houjou | G01N 21/01 382/133 |
| 2014/0141499 | A1* | 5/2014 | Nakajima | C12M 41/36 435/286.1 |

FOREIGN PATENT DOCUMENTS

| | | |
|---|---|---|
| JP | 2014-509192 A | 4/2014 |
| WO | WO 2007-099312 A1 | 9/2007 |
| WO | WO 2012/112620 A1 | 8/2012 |

OTHER PUBLICATIONS

International Search Report (ISR) (PCT Form PCT/ISA/210), in PCT/JP2017/012059, dated Jun. 27, 2017.
Uchugonova, Aisada et al., "Optical cell cleaning with NIR femtosecond laser pulses", Proc. of SPIE, 2015, vol. 9328, pp. 932819.1-932819.5.
Hohenstein, Kristi A., et al., "Laser-Based Propagation of Human iPS and ES Cells Generates Reproducible Cultures with Enhanced Differentiation Potential", Stem Cells International, 2012, vol. 2012, Article ID:926463.

* cited by examiner

CELL TREATMENT SYSTEM

TECHNICAL FIELD

The present invention relates to a cell treatment system to kill unwanted cells among cells cultured on a cell culture vessel and nurture desired cell aggregates.

BACKGROUND ART

Recently, fast growth has been witnessed in researches and developments of regenerative therapy technology and researches in drug discovery with the use of somatic stem cells, embryonic stem cells (ES cells), and induced pluripotent stem cells (iPS cells). In these researches and developments, it is crucial to be able to produce desired target cells and tissues in a large amount with high efficiency.

The process of cell culturing normally includes subculturing, which refers to the procedure of taking a cell clump out of a cell colony that has proliferated in a culture medium and then transferring the cell clump to a fresh culture medium for another round of proliferation (See following Patent Document, for example).

Currently cutting a plurality of clumps out of cells which have proliferated relies on manual operation. The cutting operation takes time and work, and besides the cutting operation can cause irregularities in the size of the clumps which result in variations in the state of growth of the subcultured cells, because it is influenced by skill of operators or other individual differences.

In regenerative therapy, cell aggregates to be transplanted for replacing or regenerating damaged tissues or organs of a patient should not contain any bad or undesired cells, otherwise rightful effect may not be exerted, moreover these cells may harm the patient's health by inducing tumorigenesis, for example. However, discarding a whole culture vessel contaminated with unwanted cells decreases the yield (the rate of harvesting) of target cells or tissues, making regenerative therapy very expensive. In order to increase the yield of target cells or tissues, it is desirable to kill or remove unwanted cells present in a culture vessel and thereby avoid wasting the other cells.

RELATED ART DOCUMENTS

Patent Documents

Patent document 1: Japanese Translation of PCT International Application Publication No. JP-T-2014-509192.

SUMMARY OF THE INVENTION

Problems to be Solved by the Invention

It is an object of the present invention to obtain cell aggregates each having a desired size more easily.

Means of Solving the Problems

According to the present invention, a cell treatment system to kill unwanted cells among cells cultured on a cell culture vessel and nurture desired cell aggregates is configured. The cell treatment system includes an imaging device to image all or a part of the cell culture vessel; an analysis unit to calculate the area or size of one or each of cell aggregates existing on the cell culture vessel based on pixel values from which the image captured by the imaging device is constituted; a display device to show the area or size of each of the cell aggregates calculated by the analysis unit on a display; a laser irradiator to emit laser toward the cell culture vessel so as to kill cells existing on the cell culture vessel; an input device to receive an operation input by a user, the operation input designating cells to be killed with irradiation of the laser or cells to survive without the irradiation of the laser among the cells existing on the cell culture vessel, or the operation input designating a position to be irradiated with the laser or a position not to be irradiated with the laser on the cell culture vessel; and a control unit to control a position irradiated with the laser emitted from the laser irradiator toward the cell culture vessel in accordance with the operation input received by the input device.

In particular, it is preferable that the analysis unit memorize an upper limit or a lower limit on the area or size of a cell aggregate and make a judgement on whether the area or size of each of the cell aggregates existing on the cell culture vessel exceeds the upper limit or the lower limit, the display device show a result of the judgement about each of the cell aggregates existing on the cell culture by the analysis unit on the display.

Also, according to the present invention, a cell treatment system to kill unwanted cells among cells cultured on a cell culture vessel and nurture desired cell aggregates is configured. The cell treatment system includes an imaging device to image all or a part of the cell culture vessel; an analysis unit to calculate the area or size of one or each of cell aggregates existing on the cell culture vessel based on pixel values from which the image captured by the imaging device is constituted, memorize an upper limit or a lower limit on the area or size of a cell aggregate, and make a judgement on whether the area or size of each of the cell aggregates existing on the cell culture vessel exceeds the upper limit or the lower limit; a laser irradiator to emit laser toward the cell culture vessel so as to kill cells existing on the cell culture vessel; and a control unit to control a position irradiated with the laser emitted from the laser irradiator toward the cell culture vessel in accordance with a result of the judgement by the analysis unit.

When the control unit controls the laser irradiator such that the laser is emitted so as to kill the cell aggregate which has the area or size smaller than the lower limit among the cell aggregates existing on the cell culture vessel, and cut the cell aggregate which has the area or size larger than the upper limit or reduce the area or size of it among the cell aggregates existing on the cell culture vessel, it is possible to equalize the size of each of the cell aggregates on the cell culture vessel.

Effects of the Invention

The present invention enables obtaining cell aggregates each having a desired size more easily.

MODE FOR CARRYING OUT THE INVENTION

Figure 1:
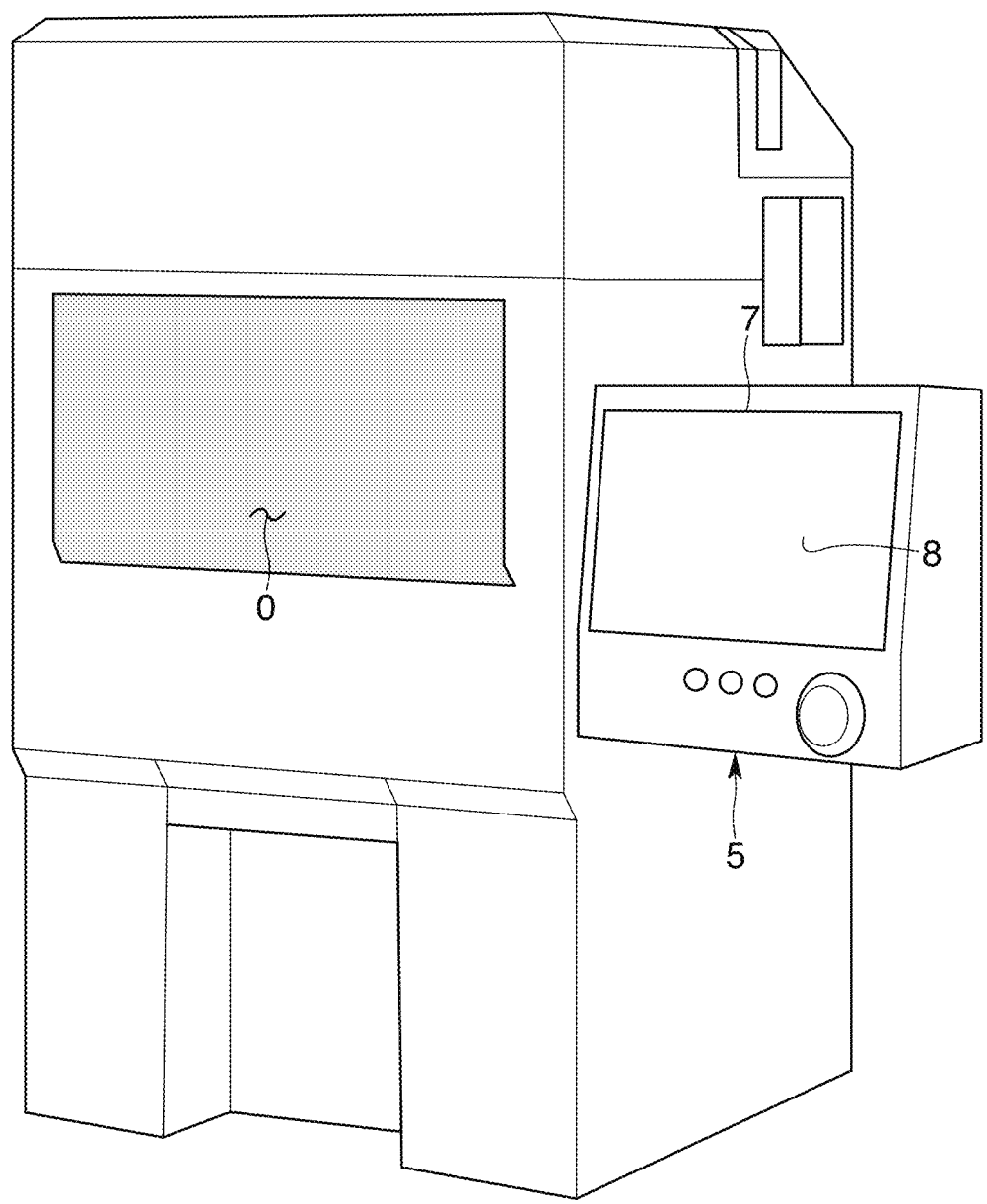
FIG. 1 is a diagram showing an exterior of a cell treatment system according to an embodiment of the present invention.

Described below is an embodiment of the present invention with reference to drawings. As shown in FIGS. 1 to 5, a cell treatment system according to the embodiment includes an imaging device 6 to image all or a part of a cell culture vessel 1 for culturing cells, an analysis unit 51 to calculate feature amounts of one or each of cell aggregates 9 existing on the cell culture vessel 1 based on the image captured by the imaging device 6, a display device 7 to show the feature amounts of each of the cell aggregates 9 calculated by the analysis unit 51 on a display to a user, a laser irradiator 3 to emit laser toward the cell culture vessel 1 so as to kill unwanted cells existing on the cell culture vessel, an input device 8 to receive an operation input by the user, and a control unit 52 to control a position irradiated with the laser emitted from the laser irradiator 3 toward the cell culture vessel 1.

Figure 3:
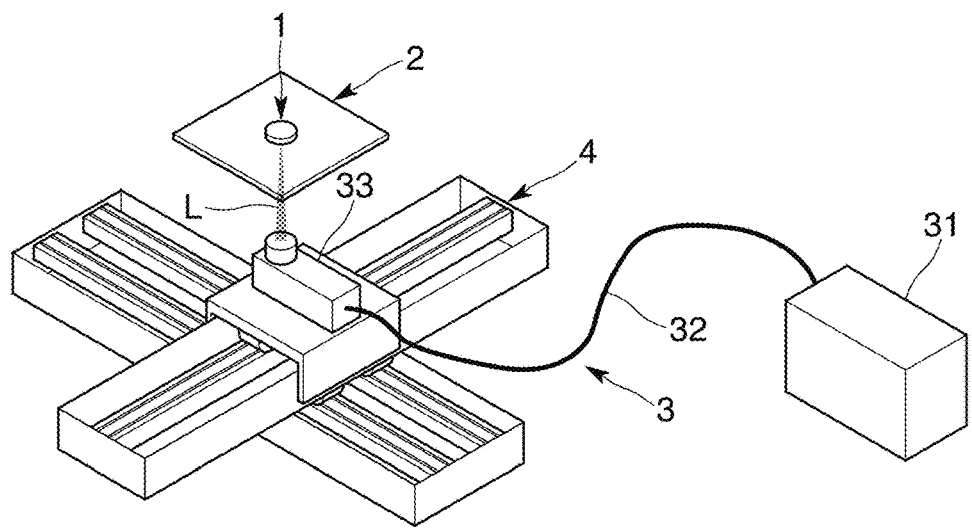
FIG. 3 is a schematic perspective view of a laser irradiator and a displacement mechanism in the cell treatment system according to the embodiment.

The laser irradiator 3 emits the laser beam L toward one or more cell culture vessels 2 supported by a support 2 so as to conduct laser processing to kill specific cells from among a group of cells cultured on the cell culture vessel 1. As shown in FIG. 3, the laser irradiator 3 has a laser source 31, a processing nozzle 33 configured to discharge the laser light L emitted from the laser source 31 toward the cell culture vessel 1, and an optical system 32 disposed between the laser source 31 and the processing nozzle 33 and configured to transfer the laser light L from the laser source 31 to the processing nozzle 33.

The laser source 31 is a device configured to oscillate a continuous-wave laser or pulsed laser L (the pulsed laser may be a high-frequency laser having a pulse width similar to that of a continuous wave). The laser L is not limited in terms of wavelength but may be a visible-light laser having such a wavelength as 405 nm, 450 nm, 520 nm, 532 nm, or 808 nm or an infrared laser, for example. It is necessary that energy of the laser L having the selected wavelength be absorbed by a to-be-irradiated layer 12 (described below) of the cell culture vessel 1. An ultraviolet laser having a wavelength of 380 nm or lower may undergo absorption by a DNA or a protein, potentially affecting cells. So, it is preferable that the wavelength of the laser L be greater than 380 nm. In this embodiment, the laser source 31 emits a continuous-wave diode laser having a wavelength near 405 nm and a maximum output of 5 W.

The processing nozzle 33 is equipped with, for example, a built-in lens that gathers the laser light L prior to irradiation of the to-be-irradiated layer 12 of the cell culture vessel 1 as well as a shutter or a mirror that switches between ON and OFF of the emission of the laser light L. The processing nozzle 33 is disposed below the cell culture vessel 1 supported on the support 2 and discharges the laser L upward. The optical axis of the laser beam L discharged from the processing nozzle 33 entries into the to-be-irradiated layer 12 of the cell culture vessel 1 at a substantially right angle.

The optical system 32 for transferring the laser L from the laser source 31 to the processing nozzle 33 may consist of any optical components such as an optical fiber, a mirror, and a lens.

A displacement mechanism 4 to control the target position in the cell culture vessel 1 where the laser beam L is to be directed principally consists of an XY stage configured to displace the processing nozzle 33 of the laser irradiator 3 relative to the cell culture vessel 1 supported on the support 2. The XY stage 4 is a known XY stage capable of quickly moving an object disposed on a linear-motor sliding platform or the like in the X-axis direction (leftward and rightward) and in the Y-axis direction (frontward and backward) with precision. In this embodiment, the processing nozzle 33 is supported on the XY stage 4 and the processing nozzle 33 is moved relative to the support 2 and the cell culture vessel 1. An alternative configuration may also be adopted where the support 2 is supported on the XY stage 4 and both the support 2 and the cell culture vessel 1 are moved relative to the processing nozzle 33. In either case, the displacement mechanism 4 allows displacement of the target position on the to-be-irradiated layer 12 of the cell culture vessel 1 where the laser L is to be directed while maintaining a substantially constant angle between the to-be-irradiated layer 12 of the cell culture vessel 1 and the optical axis of the laser beam L.

Figure 4:
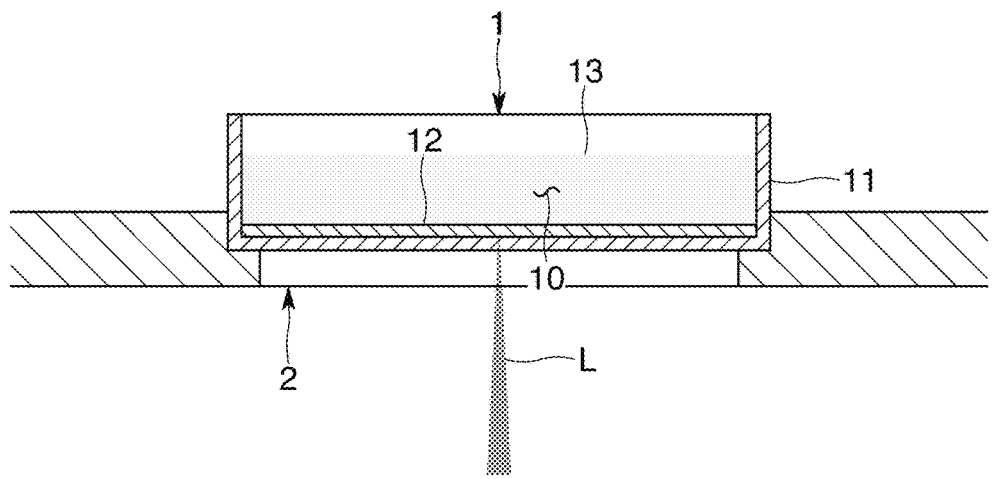
FIG. 4 is a sectional side view for describing a cell killing method performed by the cell treatment system according to the embodiment.
Figure 5:
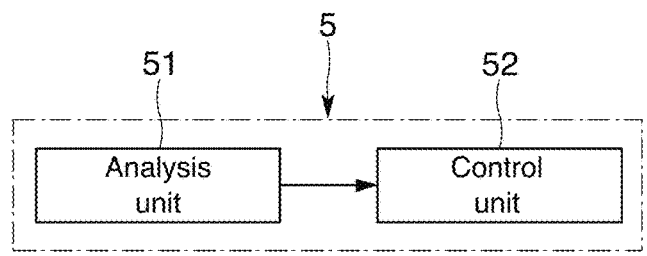
FIG. 5 is a functional block diagram of a computer in the cell treatment system according to the embodiment.

With respect to the cell culture vessel 1, referring to FIG. 4, the cell culture vessel 1 according to this embodiment comprises a main body 11 passable by the laser light L discharged from the processing nozzle 33 and the to-be-irradiated layer 12 attached to the main body 11. The to-be-irradiated layer contains a photoresponsive ingredient capable of generating heat and/or acid upon irradiation with the laser light L.

The main body 11 is made of a material, such as plastic or glass, that is transparent or light-transmissive to allow the passage of a light having a wavelength within the range of wavelength of the laser L discharged from the processing nozzle 33. Examples of the plastic include polystyrene polymers, acrylic polymers (such as poly(methyl methacrylate) (PMMA)), polyvinylpyridine polymers (such as poly (4-vinylpyridine) and 4-vinylpyridine-styrene copolymer), silicone polymers (such as polydimethylsiloxane), polyolefin polymers (such as polyethylene, polypropylene, and polymethylpentene), polyester polymers (such as poly(ethylene terephthalate) (PET) and poly(ethylene naphthalate) (PEN)), polycarbonate polymers, and epoxy polymers. The main body 11 may be a commercially-available culture vessel, which may be used as it is. In terms of shape, the main body 11 may be a dish (petri dish), a multidish, or a flask, for example, just like the shape of a commercially-available culture vessel.

The light transmittance through the main body 11 which is made of polystyrene resin is very high, as high as 85% or higher at a light wavelength of about 380 nm or greater. As the light wavelength decreases from a light wavelength of about 380 nm, the light transmittance decreases (in other words, the light absorbance by the main body 11 increases). This phenomenon is probably caused by impurities contained in the polystyrene material.

It is preferable that the to-be-irradiated layer 12 be made of a polymer (polymeric material) that contains a pigment structure (chromophore) capable of absorbing a light having a wavelength within the range of wavelength of the laser L discharged from the processing nozzle 33. This is because such a polymer can be easily applied to the main body 11 for coating, can ensure necessary adhesion of the cells, and tends not to enter into the cells. Examples of the pigment structure capable of absorbing the laser light L include derivatives of organic compounds such as azobenzene, diarylethene, spiropyrane, spirooxazines, fulgides, leucopigments, indigo, carotinoids (such as carotene), flavonoids (such as anthocyanin), and quinoids (such as anthraquinone). Examples of the polymer backbone include acrylic polymers, polystyrene polymers, polyolefin polymers, polyvinyl acetate, polyvinyl chloride, polyolefin polymers, polycarbonate polymers, and epoxy polymers.

Below is a specific example of the pigment-structure-containing polymer in the to-be-irradiated layer 12, poly [methylmethacrylate-co-(Disperse Yellow 7 methacrylate)] (Chemical Formula 1, $(C_5H_8O_2)_m(C_{23}H_{20}N_4O_2)_n$). The azobenzene in this azo polymer may be unsubstituted azobenzene or one of various modified azobenzenes modified with a nitro group, an amino group, and/or a methyl group.

the to-be-irradiated layer 12 capable of generating heat upon irradiation with the laser light L.

The light absorbance by the to-be-irradiated layer 12 which has a certain thickness and is made by coating the main body 11 with a polymer containing azobenzene as the pigment structure reaches its peak at a light wavelength of about 360 nm and then decreases as the light wavelength increases from about 360 nm. Although the light absorbance by the to-be-irradiated layer 12 at a light wavelength of about 425 nm or greater is lower than 20%, there remains a certain level of light absorbance at great light wavelengths. This phenomenon indicates that the to-be-irradiated layer 12 is well capable of absorbing the laser light L having a wavelength of 405 nm, 450 nm, 520 nm, or 532 nm.

In addition to or instead of the pigment-structure-containing polymer described above, the to-be-irradiated layer 12 may comprise a photoacid generator capable of generating an acidic substance upon irradiation with the laser light L. As disclosed in Patent Literature 1, it is preferable that a photoacid generator contain a pigment structure (chromophore) capable of absorbing a light having a wavelength within the range of wavelength of the laser L discharged from the processing nozzle 33 and also contain an acid precursor to be broken down into an acidic substance. Examples of the photoacid generator include sulfonic acid derivatives, carboxylic acid esters, onium salts, and photoacid-generating groups having a nitrobenzaldehyde structure.

Specific examples of the sulfonic acid derivatives as the photoacid generator include thioxanthone-based sulfonic

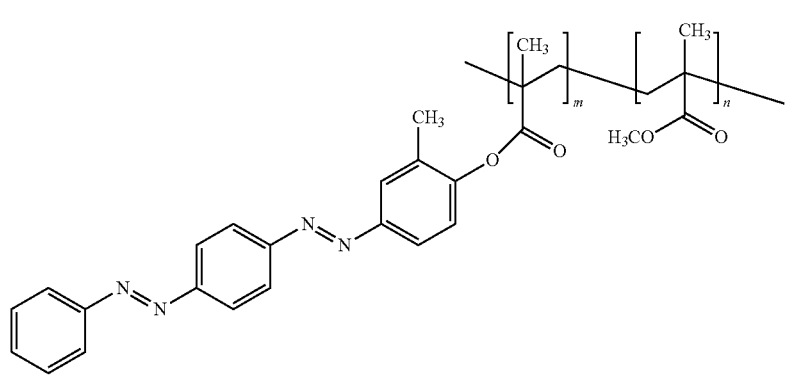

(Chemical Formula I)

By applying a raw material liquid containing the pigment-structure-containing polymer described above or a raw material liquid containing the pigment-structure-containing polymer dissolved in a solvent (such as 1,2-dichloroethane or methanol) to the upward-facing surface of the main body 11, namely the bottom of a well 10, by spin coating, casting, or other techniques and then curing the raw material liquid, the to-be-irradiated layer 12 capable of generating heat upon irradiation with the laser light L can be formed. For example, by applying a polymer containing azobenzene as the pigment structure to the upward-facing surface of the main body 11, namely the bottom of the well 10, at a density of 7 μg/cm², the to-be-irradiated layer 12 having an average thickness of 70 nm can be formed on the bottom of the well 10. Alternatively, the main body 11 may be formed by using a material blend containing a pigment capable of absorbing the laser light L or by using the pigment-structure-containing polymer, and the resulting main body 11 has the function of acid derivatives (such as 1,3,6-trioxo-3,6-dihydro-1H-11-thia-azacyclopenta[a]anthracen-2-yl sulfonate) and naphthaleneimide-based sulfonic acid derivatives (such as 1,8-naphthalimide sulfonate). In addition to these, sulfonic acid derivatives such as disulfones, disulfonyldiazomethanes, disulfonylmethanes, sulfonylbenzoylmethanes, imidesulfonates, and benzoinsulfonates may also be used.

Examples of the carboxylic acid esters include 1,8-naphthalenedicarboxylic imide methylsulfonate and 1,8-naphthalenedicarboxylic imide tosyl sulfonate. Examples of the onium salts include sulfonium salts and iodonium salts containing an anion, such as tetrafluoroborate ($BF_4$), hexafluorophosphate ($PF_6^-$), and hexafluoroantimonate ($SbF_6^-$).

By applying a raw material liquid containing a plastic (such as an acrylic polymer like PMMA or a polystyrene polymer, in particular) containing the photoacid generator or a raw material liquid containing the photoacid generator dissolved in a solvent (such as 1,2-dichloroethane or methanol) to the upward-facing surface of the main body 11, namely the bottom of the well 10, by spin coating, casting, or other techniques and then curing the raw material liquid, the to-be-irradiated layer 12 capable of generating heat and acid upon irradiation with the laser light L can be formed. For example, by applying a polymer containing a thioxanthone-based sulfonic acid derivative having a thioxanthone backbone as the pigment structure and having a sulfonic acid as the acid precursor to the bottom of the well 10 of the main body 11 at a density of 200 µg/cm$^2$, the to-be-irradiated layer 12 having an average thickness of 2 µm can be formed on the bottom of the well 10. Alternatively, the main body 11 may be formed by using a material blend containing the photoacid generator, and the resulting main body has the function of the to-be-irradiated layer 12 capable of generating heat and acid upon irradiation with the laser light L.

The light absorbance by the to-be-irradiated layer 12 which has a certain thickness and is made by coating the main body 11 with a polymer that contains a thioxanthone-based sulfonic acid derivative having a thioxanthone backbone as the pigment structure and having a sulfonic acid as the acid precursor ranges from a light wavelength of about 375 nm to a light wavelength of about 460 nm. This means that a light having a wavelength outside this range is not absorbed by the to-be-irradiated layer 12 and the laser light L having a wavelength of 405 nm or 450 nm is absorbed by the to-be-irradiated layer 12. It should be noted that the light absorbance by this to-be-irradiated layer 12 is lower than the light absorbance by the to-be-irradiated layer 12 made by using a polymer that contains azobenzene as the pigment structure, and is lower than 20% (more specifically, even lower than 10%) at a visible-light wavelength ranging from about 400 nm to about 700 nm.

It is preferable that the material of the to-be-irradiated layer 12 generate no fluorescence upon irradiation with the laser light L. It is preferable that the thickness of the to-be-irradiated layer 12 be 10 µm or lower.

The surface of the to-be-irradiated layer 12 of the cell culture vessel 1 may be coated with an ingredient capable of enhancing cell adhesion, such as an ECM (extracellular matrix) like laminin or Matrigel.

For culturing cells, the well 10 formed in the main body 11 of the cell culture vessel 1 is filled with a culture medium (particularly, a liquid culture medium) 13. In other words, the culture medium 13 is positioned directly on the to-be-irradiated layer 12 disposed at the bottom of the well 10. The cells thus cultured adhere to and proliferate on the surface of the to-be-irradiated layer 12 and form cell aggregates 9.

As shown in FIG. 4, the laser processing for killing intended cells from among a group of cells in the well 10 in the cell culture vessel 1 is conducted in the following way. The laser light L discharged from the processing nozzle 33 of the laser irradiator 3 is directed to a partial area of the to-be-irradiated layer 12 of the cell culture vessel 1 supported on the support 2 directly below the cells to be killed. In this embodiment with the processing nozzle 33 disposed below the cell culture vessel 1, the laser light L that has been discharged upward from the processing nozzle 33 passes through the main body 11 to reach the to-be-irradiated layer 12 from the back side of the to-be-irradiated layer. The built-in lens in the processing nozzle 33 focuses or directs the laser light L discharged from the processing nozzle 33 to the to-be-irradiated layer 12 of the cell culture vessel 1. The partial area of the to-be-irradiated layer 12 irradiated with the laser light L absorbs energy of the laser light L and thereby generates heat and/or acid. This heat kills unwanted cells that are present directly above the partial area.

In the case where the to-be-irradiated layer 12 comprises a photoacid generator, an acidic substance is generated in the partial area of the to-be-irradiated layer 12 irradiated with the laser light L and induces death of unwanted cells present directly above the partial area or induces detachment of these cells from the to-be-irradiated layer 12. In the case where the photoacid generator is a sulfonic acid derivative, the acidic substance thus generated is a sulfonic acid.

For example, the wavelength of the laser L is 405 nm, the output of the laser L is between 0.4 W and 5 W. Of course, the output may be over 5 W. Also, the diameter of the laser beam L is less than or equal to 50 µm. The diameter of the laser beam L may be reduced to about 20 to 25 µm. The rate of moving the processing nozzle 33 discharging the continuous-wave laser L or the high-frequency pulsed laser L which is almost like a continuous-wave laser, or the rate of moving the laser beam L, relative to the cell culture vessel 1 is set to between 50 mm/second and 2000 mm/second. When the output of the laser L is 5 W, the diameter of the laser beam L is 50 µm, and the rate of moving is 1500 mm/second, the partial area irradiated with the laser light L receives energy (energy density) of the laser light L of about 8.7 J/cm$^2$ per unit area. Even though the laser L with the above wavelength, output and energy amount cannot kill cells upon direct irradiation, the to-be-irradiated layer 12 acts to make it possible to adequately kill unwanted cells.

In order to minimize the influence of heat on cells other than cells to be killed, namely desired cells or tissues near unwanted cells, it is preferable that each of the wavelength, the output, and the energy amount of the laser light L to be applied to the to-be-irradiated layer 12 of the cell culture vessel 1 be adjusted to such a level that kills unwanted cells not instantly (i.e. the unwanted cells survive after several minutes or after ten and several minutes of the irradiation with the laser light L) but after a certain period of time (for example, after several dozen minutes or after one to several hours, typically after 60 minutes or after 120 minutes) of irradiation with the laser light L. It is actually possible to create a state where unwanted cells are alive right after irradiation with the laser light L and then are killed after a certain period of time of the irradiation.

The width or size of the area occupied by dead cells can be increased or decreased by controlling the output or the per-unit-area energy amount of the laser L. As the output and/or the per-unit-area energy amount of the laser L increases, the width or size of the area occupied by dead cells increases. In addition, it is expected that the time period after irradiation with the laser L until the death of unwanted cells decreases as the output and/or the per-unit-area energy amount of the laser L increases.

It is also preferable to irradiate the partial area of the to-be-irradiated layer 12 under the specific cells to be killed multiple times with the laser light L having the right level of output or energy amount such that the specific cells are not killed at one irradiation (the cells survive after several minutes or after ten and several minutes of the irradiation with the laser light L). In such process, it is possible to shorten the time period from the irradiation of the laser L to death of the cells and minimize the effect of heat on other cells near the specific cells.

Suitable conditions for the output and/or the per-unit-area energy amount of the laser L used in laser processing are affected by the material, the thickness, and other characteristics of the to-be-irradiated layer 12 of the cell culture vessel 1. The amount of heat generation by a unit area of the to-be-irradiated layer 12 irradiated with the laser light L through absorption of energy of the laser light L is obtained by multiplying the amount of energy per unit area of the laser light L applied to the to-be-irradiated layer 12 by a factor of light utilization. The factor of light utilization refers to the rate at which a unit area of the to-be-irradiated layer 12 absorbs and utilizes energy of the laser light L. The factor of light utilization depends not only on the characteristics of (more specifically, the light absorbance by) the material of the to-be-irradiated layer 12 but also on the amount of a certain ingredient (per unit area of the to-be-irradiated layer 12) contributing to photo-thermal reaction in which heat is generated upon absorption of the laser light L. When the coating thickness of the material that forms the to-be-irradiated layer 12 of the main body 11 increases, the amount of the ingredient contributing to photo-thermal reaction increases accordingly, leading to an increase in the factor of light utilization of the to-be-irradiated layer 12 per unit area. Such an increase in the factor of light utilization leads to an increase in the amount of heat generation by a unit area of the to-be-irradiated layer 12, facilitating cell death. In view of the circumstances above, it is required that the factor of light utilization by the to-be-irradiated layer 12 of the cell culture vessel 1 be considered and the output and/or the per-unit-area energy amount of the laser L suitable for killing unwanted cells be experimentally determined.

The imaging device 6 obtains an image of the cultured cells or the cell aggregates 9 on the cell culture vessel 1 through a phase-contrast microscope, for example, and captures the image with a solid-state imaging device (image sensor) such as CCD or CMOS.

The display device 7 is a known liquid-crystal display or the like. The input device 8 is a pointing device such as touchscreen, trackpad and mouse, a keyboard, push buttons, and so on that a user can operate with fingers. A touchscreen as the input device 8 may be layered on the display device 7.

It is preferable that at least the processing nozzle 33, the cell culture vessel 1 in the laser processing and the support 2 be disposed within a processing chamber 0 with an internal atmosphere equivalent to that of a $CO_2$ incubator. The $CO_2$ incubator is a well-known device with its internal atmosphere being controllable in terms of $CO_2$ concentration and temperature. It is used in order to maintain a suitable cell-culturing environment, such as a suitable pH level of the culture medium in the cell culture vessel 1. Imaging of the cell culture vessel 1 by the imaging device 6 can be carried out inside or outside the processing chamber 0.

Figure 2:
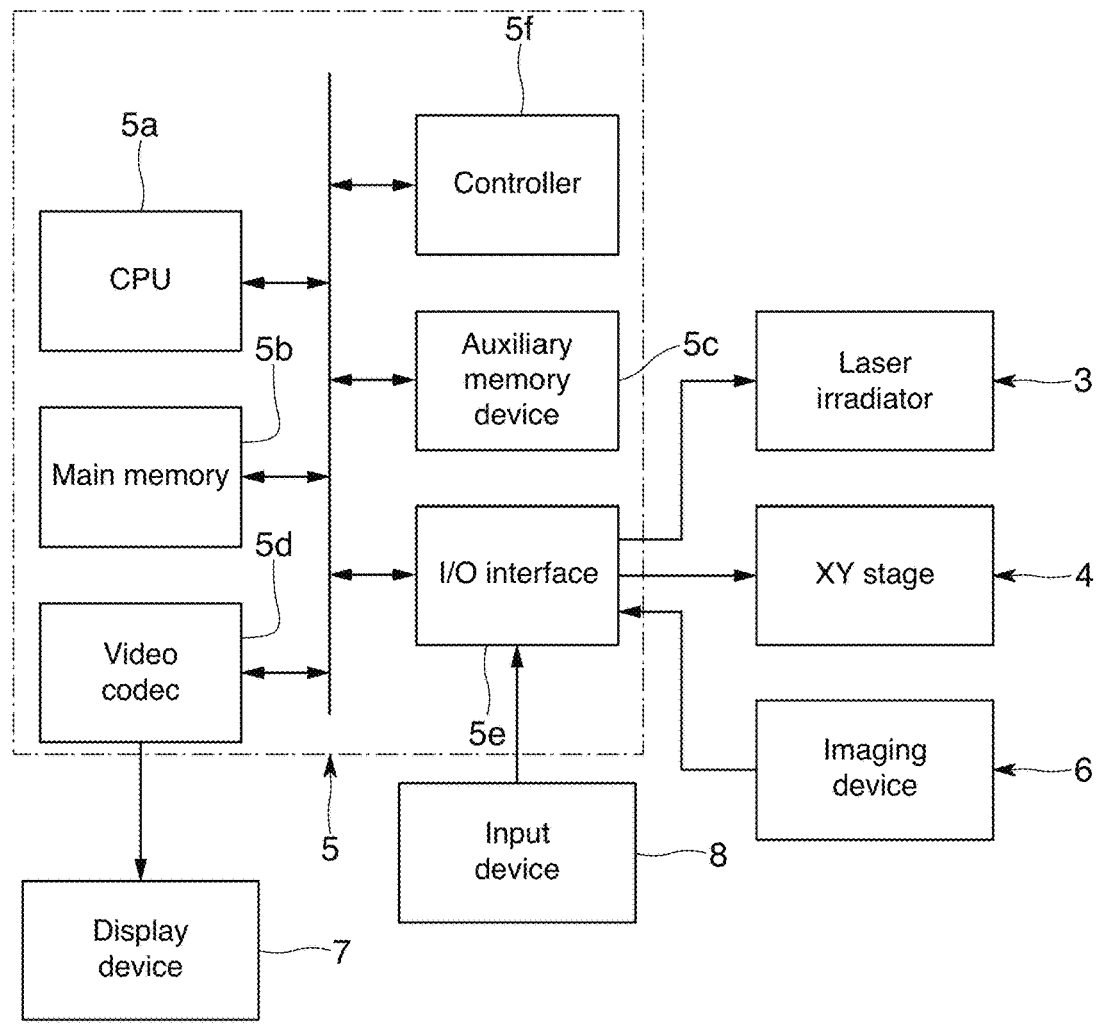
FIG. 2 is a diagram showing a configuration of hardware resources in the cell treatment system according to the embodiment.

The analysis unit 51 and the control unit 52 are constituted by a computer 5, for example, a general-purpose personal computer, a server computer, a workstation, or analogous computers. As shown in FIG. 2, this computer 5 consists of components such as a CPU 5a, a main memory 5b, an auxiliary memory device 5c, a video codec 5d, and an I/O interface 5e. Each of these components is controlled by a controller (i.e. a system controller, an I/O controller, and so on) 5f to operate in coordination with the other components. The auxiliary memory device 5c is a flash memory or a hard drive, for example. The video codec 5d is composed of a graphics processing unit (GPU) which creates images to be displayed based on instructions from the CPU 5a and outputs video signals corresponding to the images to the display device 7. A video memory which temporarily stores data of the images or screen, and so on. The I/O interface 5e is a device to communicatively connect with and control the laser source 31, the XY stage 4, the input device 8, the imaging device 6, and so on. The I/O interface 5e may contain a servo driver (servo controller).

Programs to be run by the computer 5 is stored in the auxiliary memory device 5c. To run the programs, the main memory 5b reads those and then the processor 5a interprets those. According to the programs, the computer 5 functions as the analysis unit 51 and the control unit 52 in this cell culture system.

The analysis unit 51 detects the location and region of one or each of the cell aggregates 9 shown in the image captured by the imaging device 6, that is, the cell aggregates 9 existing on the cell culture vessel 1 which is the object of imaging, based on pixel values from which the image is constituted. Then the analysis unit 51 calculates the feature amounts of each of the cell aggregates 9, at least the area or size (diameter or the like) of each of the cell aggregates 9. When calculating the size of the cell aggregate 9, the analysis unit 51 may compute the maximum width (in other words, major axis) or the minimum width (in other words, minor axis) of the cell aggregate 9. In addition, the analysis unit 51 can calculate another feature amounts of each of the cell aggregates 9 existing on the cell culture vessel 1 based on the pixel values of the image, for example, the transmittance of each of the cell aggregates 9, the measure of the shape of each of the cell aggregates 9 shown in the image such as roundness, density of cells of each of the cell aggregates 9.

Also, the analysis unit 51 can determine what kind of cells each of the cell aggregates 9 shown in the image contains, which is one of the feature amounts of the cell aggregates 9 existing on the cell culture vessel 1, based on the pixel values of the image, and the analysis unit 51 can discriminate desired cells to be cultured (or unwanted cells other than target cells) existing on the cell culture vessel 1 or discriminate between a part that target cells constitute and a part that unwanted cells constitute in each of the cell aggregates 9.

Nowadays a fluorescent marker having low cytotoxicity (a lectin probe, rBC2LCN, which binds to glycans on the surface of undifferentiated cells) to be added to the culture medium filled into the cell culture vessel 1 so as to stain undifferentiated ES cells or undifferentiated iPS cells alive without being fixed on the cell culture vessel 1 is already known. This fluorescent marker makes it possible to stain undifferentiated ES cells or undifferentiated iPS cells that are target cells in culturing ES cells or iPS cells existing on the cell culture vessel 1. Imaging the cell culture vessel 1 in a state where target cells are stained by the imaging device and analyzing the captured image reveals the location and region of the target cells and unwanted cells (for example, differentiated cells) other than the target cells, thereby the area, size, roundness, and so on, of those cell aggregates 9 can be calculated. Incidentally, a stripping solution to strip a rBC2LCN lectin from undifferentiated cells is existent, it is possible to continue culturing the undifferentiated cells from which the rBC2LCN lectin is stripped.

Of course, it is possible to detect the location and region of desired target cells and the location and region of unwanted cells with not using dyestuffs to dye target cells or unwanted cells but using known image-analysis algorithm. It is available to increase accuracy in determining types of cells shown in the image through learning by artificial intelligence.

When the analysis unit 51 discriminates target cells existing on the cell culture vessel 1 or discriminates between a part that target cells constitute and a part that unwanted cells constitute in each of the cell aggregates 9, it is preferable in calculating the feature amounts, namely, the area or size, transmittance, roundness, and so on, of each of the cell aggregates 9 to detect only the part of the objective cell aggregate 9 that is occupied by the target cells and obtain the area or size, transmittance, roundness, and so on, of that part.

Further, the analysis unit 51 stores proper upper limits and/or proper lower limits on the feature amounts of the cell aggregates 9 in a necessary memory area of the main memory 5c or the auxiliary memory device 5c. Hence, the analysis unit 51 makes a judgement on whether the feature amounts of each of the cell aggregates 9 on the cell culture vessel 1 obtained through the image analysis exceeds the upper limit and/or the lower limit.

Figure 6:
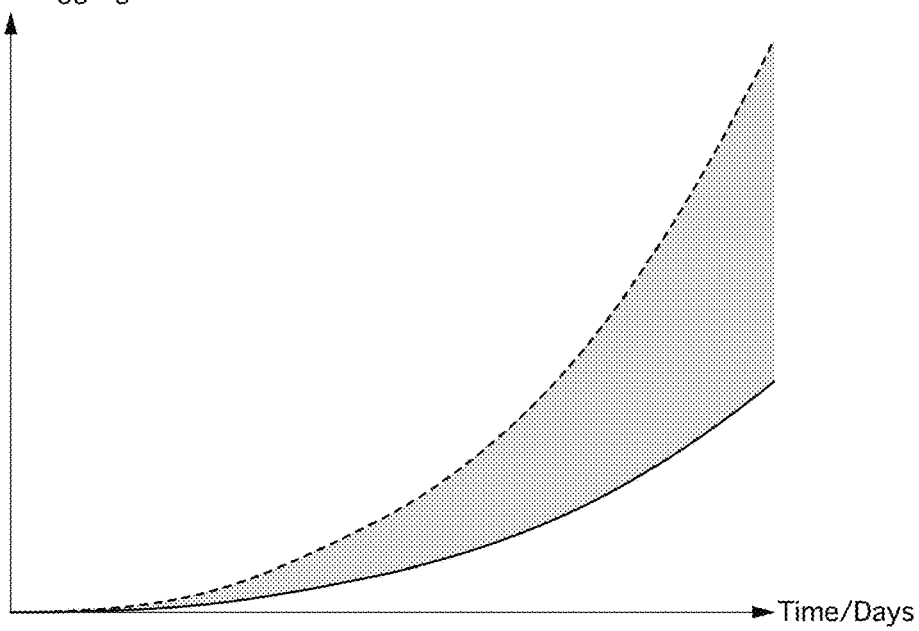
FIG. 6 is a graph showing the relationship of time which elapses from a beginning of culturing with the area or size of a normal cell aggregate.

In the process for culturing desired target cells and yielding the cell aggregates 9 (or clumps) of those, a regular relationship exists between culture time which is a time (or days) that elapses since the start of the culturing and the normal area or size of each of the cell aggregates 9 of the target cells at a point in time after the elapse of the culture time. FIG. 6 conceptually shows the relationship between the culture time since the start of the culturing and the normal area or size of the cell aggregate 9. In FIG. 6, the solid line represents the lower limit of the proper range on the area or size of the cell aggregate 9, the dot-dash line represents the upper limit of the proper range on the area or size of the cell aggregate 9. A region marked with halftone dots indicates the proper range of the area or size of the cell aggregate 9. The upper limit and the lower limit on the normal area or size of the cell aggregate 9 may vary depending on the culture time.

It is desirable not to use the cell aggregates 9 which have an area or size deviating from the proper range according to the culture time for the next step after culturing on the cell culture vessel 1 such as subculturing and induction of differentiation. The cell aggregates 9 with an area or size smaller than the lower limit of the proper range can be bad aggregates 9 in which the cells have not successfully proliferated and which have not grown in accordance with the culture time. On the other hand, the cell aggregates 9 with an area or size larger than the upper limit of the proper range grows excessively fast beyond supposition, although the cells proliferates themselves. Using these cell aggregates 9 for the next subculture or induction of differentiation may cause irregularity in conditions of growth of subcultured or differentiated cells.

Therefore, with respect to each of the cell aggregates 9 on the cell culture vessel 1, the analysis unit 51 makes a judgement on whether the area or size of the cell aggregate 9 calculated through the image analysis deviates from the proper range according to the culture time, and indicates that it is to be spared, it is to be killed, or it is to be cut or trimmed. In principle, the cell aggregate 9 with an area or size in the proper range is to be spared. The cell aggregate 9 with an area or size smaller than the lower limit is bad and to be killed. In contrast, the cell aggregate 9 with an area or size larger than the upper limit is to be cut into a plurality of cell aggregates 9 which have an area or size in the proper range each, or to be reduced in the area or size by killing the cells that are part of the cell aggregate 9 (in particular, the cells in the peripheral part of the cell aggregate 9).

Figure 7:
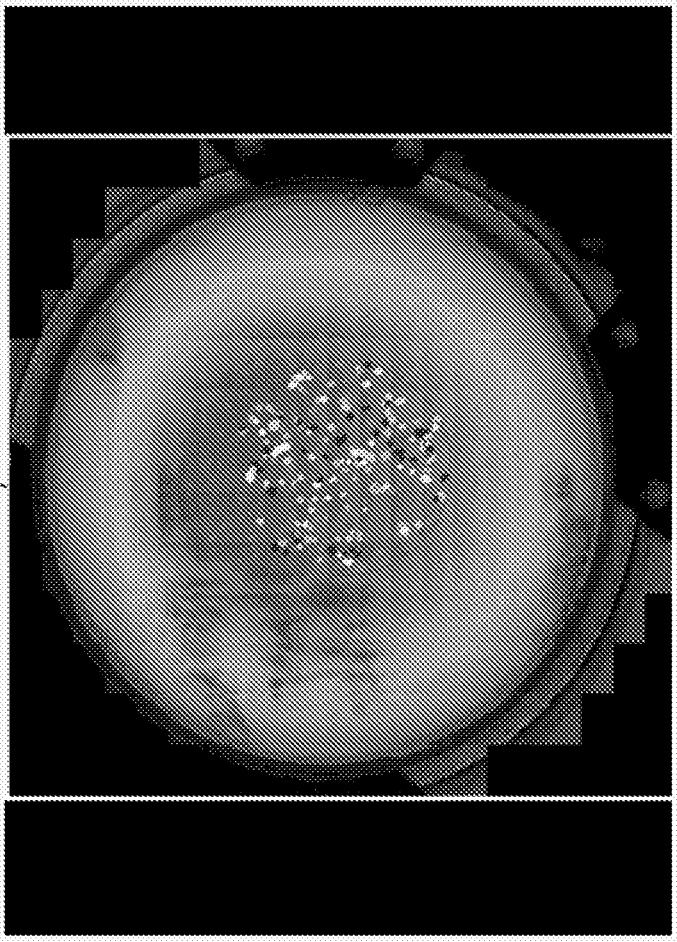
FIG. 7 is a diagram showing an example of displaying the feature amount of each of cell aggregates by the cell treatment system according to the embodiment.
Figure 8:
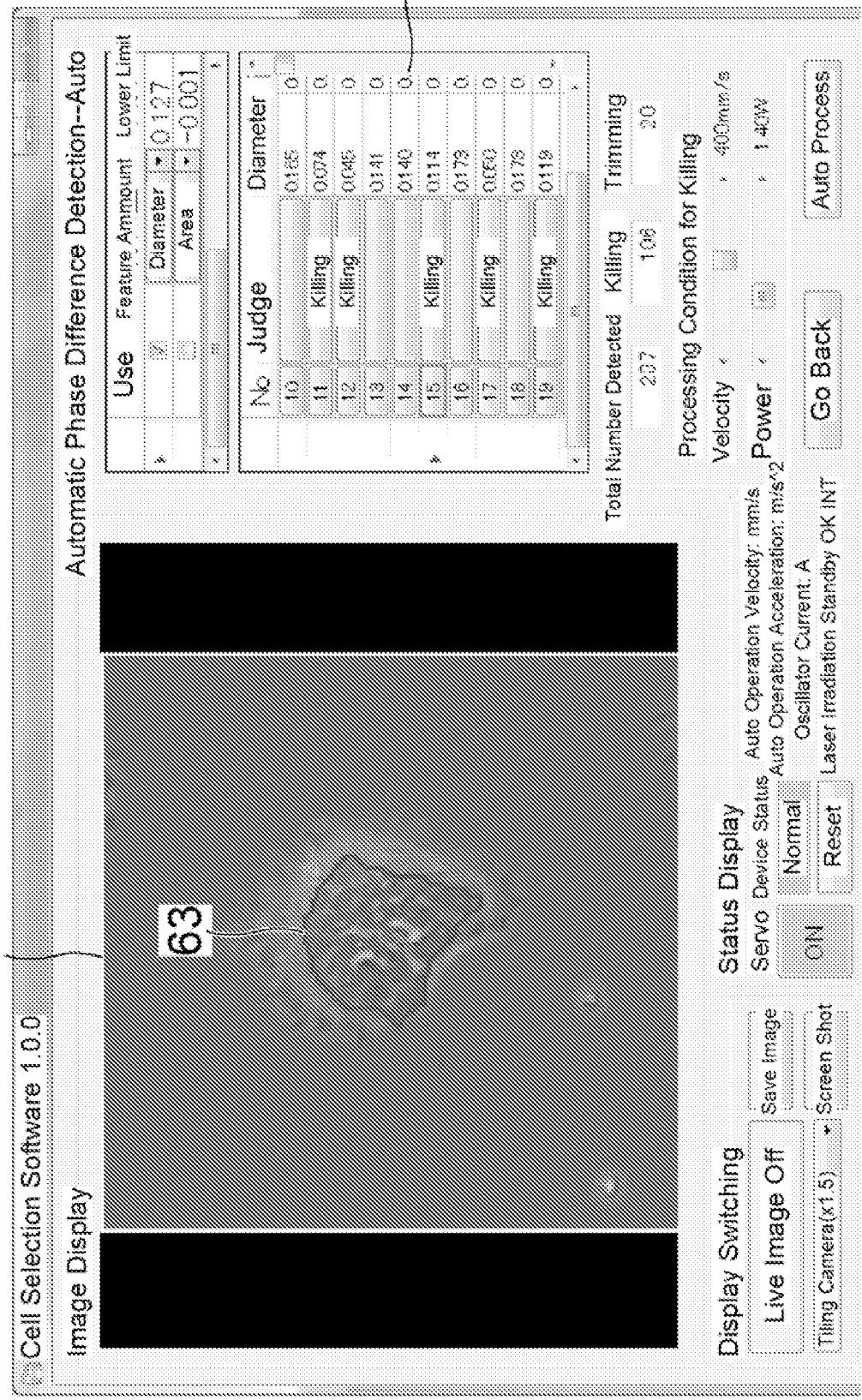
FIG. 8 is a diagram showing an example of displaying the feature amount of each of cell aggregates by the cell treatment system according to the embodiment.
Figure 9:
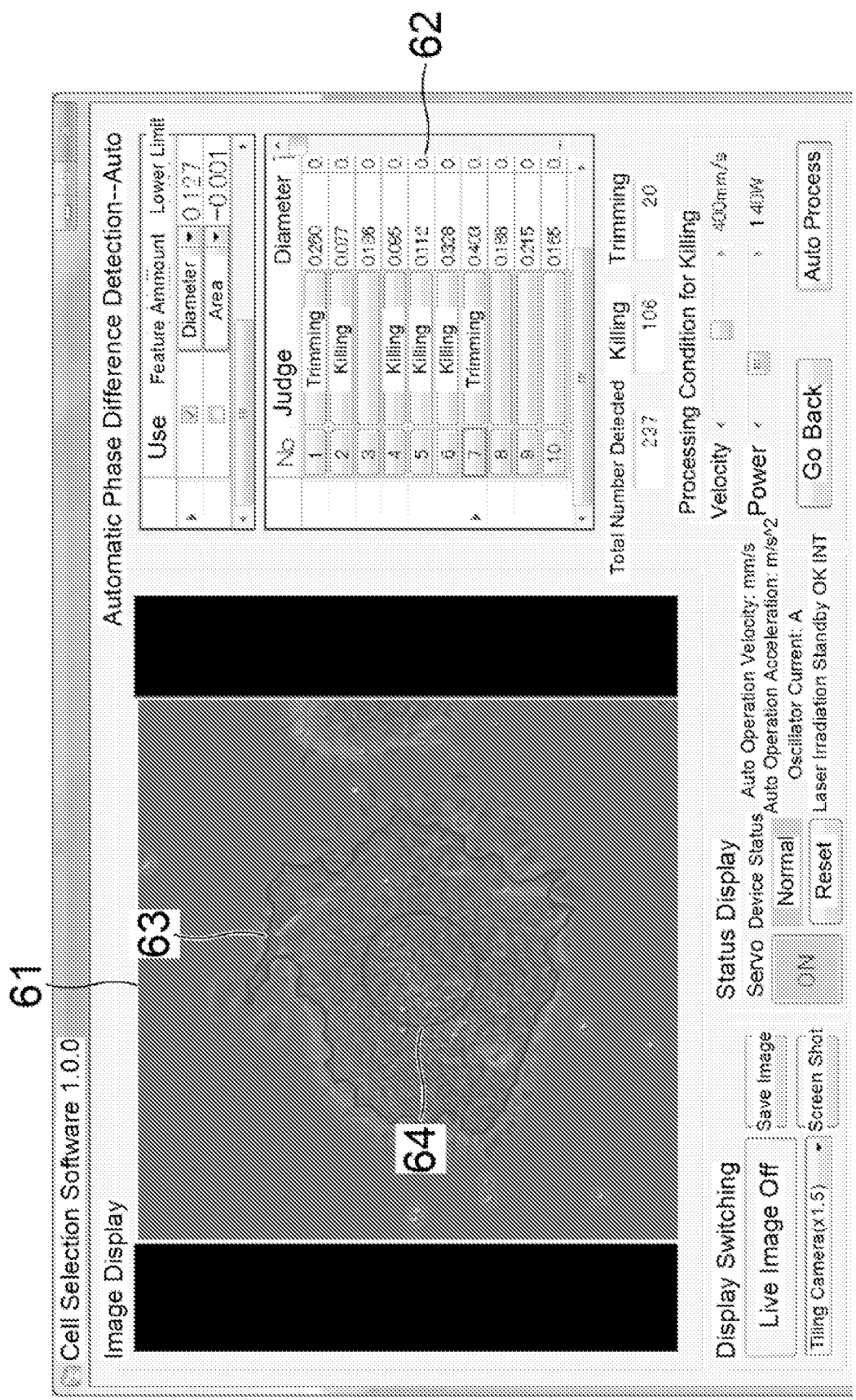
FIG. 9 is a diagram showing an example of displaying the feature amount of each of cell aggregates by the cell treatment system according to the embodiment.

The computer 5 displays information containing the feature amounts of each of the cell aggregates 9 existing on the cell culture vessel 1 analyzed by the analysis unit 51 on the display device 7. FIGS. 7 to 9 shows examples of displaying the feature amounts of each of the cell aggregates 9. In the example shown in FIG. 7, the image of the whole cell culture vessel 1 and the locations of the many cell aggregates 9 existing on the cell culture vessel 1 are displayed inside a left area 61. Also, with respect to the cell aggregates 9 on the cell culture vessel 1, a list of sizes (or diameters) of the cell aggregates 9 and results of the judgement on whether the size of each of the cell aggregate 9 is in the proper range ("kill" means that the diameter of the cell aggregate 9 is smaller than the lower limit, "trim" means that the diameter of the cell aggregate 9 is larger than the upper limit) is displayed inside a right area 62.

In the example shown in FIGS. 8 and 9, an enlarged image of one cell aggregate 9 chosen among the cell aggregates 9 existing on the cell culture vessel 1 by the user is displayed in the left area 61. A drawn contour 63 superimposed on this enlarged image is an outer edge of the region recognized as the cell aggregate 9 by the analysis unit 51 through analyzing the captured image of the cell culture vessel 1. The input device 8 receives an operation input to choose which cell aggregate 9 should be displayed into an enlarged image by the user. FIG. 8 shows the example of displaying the cell aggregate 9 which has a size smaller than the lower limit and is to be killed, FIG. 9 shows the example of displaying the cell aggregate 9 which has a size larger than the upper limit and is to be cut or trimmed. A circle 64 drawn within the contour 63 in the left area 61 in FIG. 9 is an expected size of a cell aggregate 9 obtained as a result of carrying out a trim such that cells on the periphery of the objective cell aggregate 9 (or outside the circle 64) are killed. In short, the contour 63 and the circle 64 represent a range of the trim to kill the cells.

When the analysis unit 51 calculates the feature amounts other than the area or size of the cell aggregates 9 existing in the cell culture vessel 1, for example, roundness and density of cells of the cell aggregates 9, the roundness of each of the cell aggregates 9 and so on can be displayed on the display device 7.

In addition, when the analysis unit 51 discriminates the target cells existing on the cell culture vessel 1 or discriminates between a part that the target cells constitute and a part that the unwanted cells constitute in each of the cell aggregates 9, it is preferable to display the location where the target cells exist or the unwanted cells exist in a visible manner for the user.

It is possible to set judgment conditions used by the analysis unit 51 arbitrarily. The analysis unit 51 can judge that each of the cell aggregates 9 is to be spared, to be killed, or to be cut or trimmed, based on any judgment conditions, for example, comparison of the transmittance of the cell aggregate 9 with the upper limit thereof and/or the lower limit thereof, comparison of the roundness of the cell aggregate 9 with the upper limit thereof and/or the lower limit thereof, comparison of the density of cells of the cell aggregate 9 with the upper limit thereof and/or the lower limit thereof, and whether the cells are the target cells or not, other than the condition that the area or size of the cell aggregate 9 is larger than the upper limit and/or is smaller than the lower limit.

Moreover, the analysis unit 51 can judge that the objective cell aggregate 9 is to be spared, to be killed, or to be cut or trimmed, based on a combination of a plurality of judgment conditions about the cell aggregates 9. For example, the analysis unit 51 may determine the cell aggregate 9 is to be spared on the AND condition that the area or size of the cell aggregate 9 is within the proper range from the lower limit to the upper limit and besides the roundness of the cell aggregate 9 is within the proper range from the lower limit to the upper limit. Also, the analysis unit 51 may determine the cell aggregate 9 is to be spared on the OR condition that the area or size of the cell aggregate 9 is within the proper range from the lower limit to the upper limit or the cells constituting the cell aggregate 9 are clearly the target cells.

The control unit 52 controls a position irradiated with the laser L emitted from the processing nozzle 33 of the laser irradiator 3 toward the cell culture vessel 1. As mentioned above, in order to kill intended cells from among a group of the cells or the cell aggregates 9 existing on the cell culture vessel, it is necessary to irradiate only the partial area of the to-be-irradiated layer 12 under the cells to be killed. There are several ways to determine where to be irradiated with the laser light L in the cell culture vessel 1:

(I) The user who sights the image or information displayed on the display device 7 determines the position or area to be irradiated or not to be irradiated with the laser L in the cell culture vessel 1. The input device 8 receives an operation input to designate the position or area to be irradiated or not to be irradiated with the laser L by the user. If the user designates the position or area not to be irradiated, the other position or area should be irradiated with the laser L.

(II) The user who sights the image or information displayed on the display device 7 determines the cells or the cell aggregates 9 to be killed with the laser L irradiation or to be spared without the laser L irradiation among the cells or the cell aggregates 9 existing on the cell culture vessel 1. The input device 8 receives an operation input to designate the cells or the cell aggregates 9 to be killed or to be spared by the user. If the user designates the cells or the cell aggregates 9 to be spared, the area other than the area occupied by the designated cells or cell aggregates 9 in the cell culture vessel 1 should be irradiated with the laser L.

(III) The computer 5 determines the position or area to be irradiated or not to be irradiated with the laser L in the cell culture vessel 1 in accordance with a result of the judgement by the analysis unit 51. The analysis unit 51 judges that, among the cell aggregates 9 existing on the cell culture vessel 1, ones having an area or size within the proper range from the lower limit to the upper limit are to be spared, ones having an area or size smaller than the lower limit are to be killed, and ones having an area or size larger than the upper limit are to be cut or trimmed. When the roundness of the shape of each of the cell aggregates 9 is calculated, the analysis unit 51 judges that the cell aggregate 9 with the roundness smaller than the lower limit stored in the main memory 5b or the auxiliary memory device 5c is to be killed, or to be trimmed so that the cells on the periphery are killed and the shape of the cell aggregate 9 gets similar to a perfect circle. When the density of cells of each of the cell aggregates 9 is calculated, the analysis unit 51 judges that the cell aggregate 9 with the density smaller than the lower limit stored in the main memory 5b or the auxiliary memory device 5c or larger than the upper limit stored in it is to be killed. The upper limit and/or the lower limit on the roundness, density of cells, and so on of the normal cell aggregate 9 may vary depending on the time that elapses since the start of culturing the cells. Also, when the types of the cells or the cell aggregates 9 existing on the cell culture vessel 1 are determined through the image analysis, the analysis unit 51 judges that the desired target cells are to be spared and the unwanted cells other than those are to be killed. As mentioned above, the analysis unit 51 can judge that the objective cell aggregate 9 is to be spared, to be killed, or to be cut or trimmed, based on a combination of a plurality of conditions, that is an AND condition or an OR condition, about the feature amounts of the cell aggregates 9.

In the cell treatment system according to the embodiment, any of the above (I), (II) and (III) can be adopted. The control unit 52 acquires one or multiple sets of X-Y coordinates belonging on the position or in the area which is designated to be irradiated with the laser L by the user's own hand in the cell culture vessel 1. Otherwise the control unit 52 acquires one or multiple sets of X-Y coordinates belonging in the area which is determined to be irradiated with the laser L on the basis of the possibility that the unwanted cells or other cells to be killed exist in the area, in other words, the area is not occupied by the cell aggregates 9 of the target cells to be spared in the cell culture vessel. Then the control unit 52 temporarily stores the X-Y coordinates of the target positions to be irradiated in the main memory 5b or the auxiliary memory device 5c.

Figure 10:
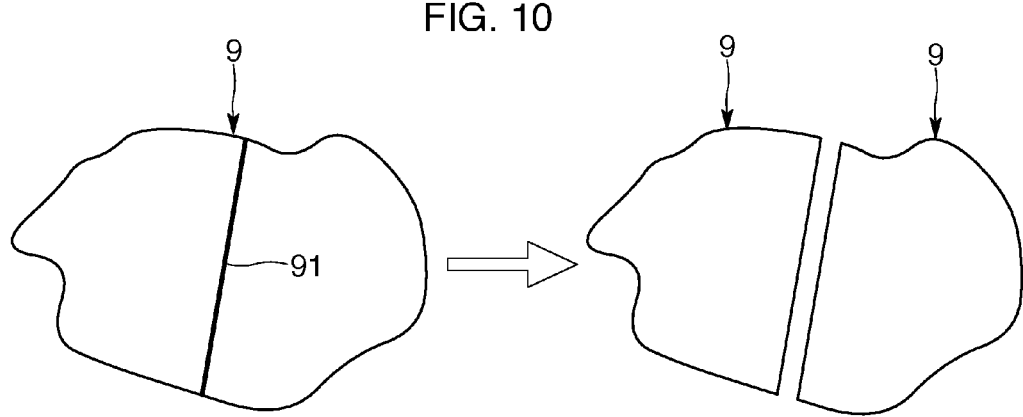
FIG. 10 is a plan view showing the progress of cutting a cell aggregate by the cell treatment system according to the embodiment.

When cutting the cell aggregate 9 with a large area or size and making the cell aggregate 9 with a smaller area or size, as shown in FIG. 10, the laser L is applied to a partial area of the to-be-irradiated layer 12 in the cell culture vessel 1 directly below the boundary 91 by which the objective cell aggregate 9 is divided into a plurality of portions so as to kill the cells on the boundary 91. To do that, the control unit 52 acquires multiple sets of X-Y coordinates on the boundary 91 to be irradiated with the laser L.

Figure 11:
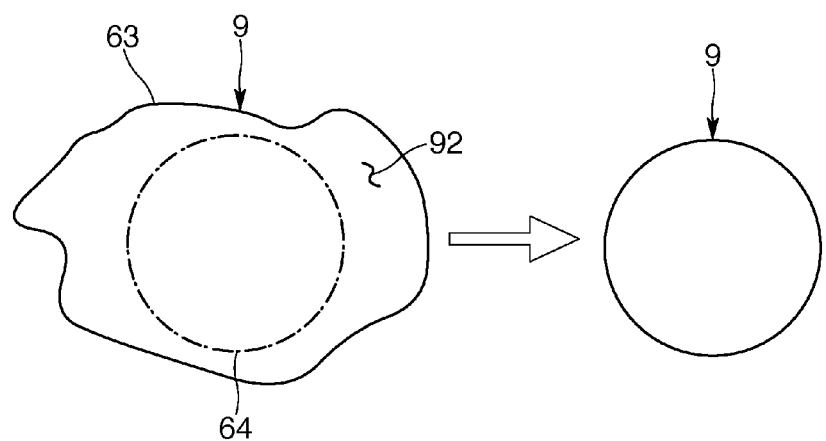
FIG. 11 is a plan view showing the progress of trimming a cell aggregate by the cell treatment system according to the embodiment.

When trimming, that is, killing the cells on the periphery of the cell aggregate 9 and making the cell aggregate 9 with a smaller area or size or with a higher roundness, as shown in FIG. 11, the laser L is applied to a partial area of the to-be-irradiated layer 12 in the cell culture vessel 1 directly below the periphery 92 so as to kill the cells on the periphery. To do that, the control unit 52 acquires multiple sets of X-Y coordinates belonging in the periphery 92 to be irradiated with the laser L.

The control unit 52 is configured to control the ON-OFF state of the discharge of the laser L from the processing nozzle 33 toward the to-be-irradiated layer 12 of the cell culture vessel 1 and to control the output intensity of the laser L irradiating the to-be-irradiated layer 12, namely the amount of energy of the laser L. More specifically, the control unit 52 provides the processing nozzle 33 via the I/O interface 5e with a command signal for switching between ON and OFF of the discharge of the laser L from the processing nozzle 33 and also provides the processing nozzle 33 or the laser source 31 via the I/O interface 5e with a control signal for controlling the output of the laser L.

Further, the control unit 52 is configured to operate the XY stage 4 supporting the processing nozzle 33 so as to move the processing nozzle 33 toward the X-Y coordinates of the target position to be irradiated with the laser L, thereby directing the optical axis of the laser beam L discharged from the processing nozzle 33 to the X-Y coordinates. More specifically, the control unit 52 provides the XY stage 4 via the I/O interface 5e with a command signal related to the X-Y coordinates of the target position. By discharging the continuous-wave laser L or the high-frequency pulsed laser L, which is almost like a continuous-wave laser, from the processing nozzle 33 while moving the processing nozzle 33 and thereby moving the laser beam L according to the X-Y coordinates of the target position that are changing with time, the target position where the laser L is to be directed can be continuously moved while the to-be-irradiated layer 12 of the cell culture vessel 1 is being irradiated. The control unit 52 performs an operation such that the processing nozzle 33 is moved relative to the cell culture vessel 1 in a fashion similar to raster scanning with the optical axis of the processing nozzle 33 moving across the area determined by the user or other than the area where the cell aggregates 9 to be spared occupy on (the to-be-irradiated layer 12 of) the cell culture vessel 1, and then the processing nozzle 33 discharges the laser L when the optical axis of the processing nozzle 33 has reached directly below the specific cells to be killed. Consequently the state where the unwanted cells in the above area are died and only the cell aggregates 9 of the desired target cells are alive on the cell culture vessel 1 is achieved.

The cell treatment system according to this embodiment contributes to obtaining the cell aggregates 9 of the target cells each having a regular size surely at a point when a regular time elapses since the start of culturing the target cells. For example, it requires about seven days to proceed from the start of culturing with using the cell culture vessel 1 to the end thereof, that is, undertaking passage or induction of differentiation. In the middle of the culture time of seven days, this cell treatment system culls slow-growing bad cells, and cuts or trims fast-growing cell aggregates 9 to reduce the size thereof. Thereby it is possible to surely obtain the iPS cell aggregates 9 suitable for subculturing at a point after seven days since the start of culturing.

In so doing, since the cell aggregates 9 are notably small for about two days after seeding iPS cells in the cell culture vessel 1, the process of culling, cutting or trimming the cell aggregates 9 through imaging the cell culture vessel 1, analyzing and applying the laser L by the cell treatment system should be begun at a point when three days elapses since the start of culturing. In addition, as the days elapse since the start of culturing the cells, the number of the cells in the cell culture vessel 1 increases and the proliferation of the cells is exponentially accelerated. Hence, it is preferable to shorten the cycle of culling, cutting or trimming the cell aggregates 9 through imaging the cell culture vessel 1, analyzing and applying the laser L in proportion as the elapsed time since the start of culturing increases.

After a necessary culture time elapses, it is possible to float and retrieve the cell aggregates 9 by, for example, adding culture solution or other liquid to the well 10 of the cell culture vessel 1 (or pouring culture solution or other liquid over the cell aggregates 9). Using an enzyme to detach the cells adhering to the cell culture vessel 1 from its surface is not required, however, the enzyme is usable.

In this embodiment, the cell treatment system to kill the unwanted cells among the cells cultured on the cell culture vessel 1 and nurture the desired cell aggregates 9 is configured, the cell treatment system includes the imaging device 6 to image all or a part of the cell culture vessel 1; the analysis unit 51 to calculate the area or size of one or each of the cell aggregates 9 existing on the cell culture vessel 1 based on the pixel values from which the image captured by the imaging device 6 is constituted; the display device 7 to show the area or size of each of the cell aggregates 9 calculated by the analysis unit 51 on the display; the laser irradiator 3 to emit laser L toward the cell culture vessel 1 so as to kill the cells existing on the cell culture vessel 1; the input device 8 to receive the operation input by the user, the operation input designating the cells to be killed with the irradiation of the laser L or the cells to survive without the irradiation of the laser L among the cells existing on the cell culture vessel 1, or the operation input designating the position to be irradiated with the laser L or the position not to be irradiated with the laser L on the cell culture vessel 1; and the control unit 52 to control the position irradiated with the laser L emitted from the laser irradiator 3 toward the cell culture vessel 1 in accordance with the operation input received by the input device 8.

The analysis unit 51 memorizes the upper limit or the lower limit on the area or size of the cell aggregate 9 and makes a judgement on whether the area or size of each of the cell aggregates 9 existing on the cell culture vessel 1 exceeds the upper limit or the lower limit. The display device 7 shows the result of the judgement about each of the cell aggregates 9 existing on the cell culture vessel 1 by the analysis unit 51 on the display.

Also, in this embodiment, the cell treatment system to kill the unwanted cells among the cells cultured on the cell culture vessel 1 and nurture the desired cell aggregates 9 is configured, the cell treatment system includes the imaging device 6 to image all or a part of the cell culture vessel 1; the analysis unit 51 to calculate the area or size of one or each of the cell aggregates 9 existing on the cell culture vessel 1 based on the pixel values from which the image captured by the imaging device 6 is constituted, memorize the upper limit or the lower limit on the area or size of the cell aggregate 9, and make a judgement on whether the area or size of each of the cell aggregates 9 existing on the cell culture vessel 1 exceeds the upper limit or the lower limit; the laser irradiator 3 to emit laser L toward the cell culture vessel 1 so as to kill the cells existing on the cell culture vessel 1; and the control unit 52 to control the position irradiated with the laser L emitted from the laser irradiator 3 toward the cell culture vessel 1 in accordance with the result of the judgement by the analysis unit 51.

The control unit 52 controls the laser irradiator 3 such that the laser L is emitted so as to kill the cell aggregate 9 which has the area or size smaller than the lower limit among the cell aggregates 9 existing on the cell culture vessel 1, and cut the cell aggregate 9 which has the area or size larger than the upper limit or reduce the area or size of it among the cell aggregates 9 existing on the cell culture vessel 1.

It is possible for the user to arbitrarily set the upper limit and/or the lower limit to be compared with the feature amount (i.e. the area or size, roundness density of cells, and so on) of each of the cell aggregates 9 existing on the cell culture vessel 1. The computer 5 which functions as the analysis unit 51 receives an input of the upper limit and/or the lower limit by the user via the input device 8, stores the upper limit and/or the lower limit in the main memory 5b or the auxiliary memory device 5c, and uses it for the judgement about each of the cell aggregates 9 on the cell culture vessel 1.

The cell treatment system according to the embodiment enables obtaining the cell aggregates 9 each having a desired size more easily and stably when a predetermined culture time elapses.

The present invention is not limited to the above-described embodiment. The wavelength of the laser L for laser processing to kill unwanted cells is not limited to 405 nm. In the case where the laser L having a different wavelength is used, the to-be-irradiated layer 12 of the cell culture vessel 1 needs to be made by using an ingredient (particularly, a polymer) having a pigment structure capable of absorbing a light having that wavelength. In the case where a near-infrared laser L having a wavelength of 808 nm or 1064 nm is used, for example, a phthalocyanine (a phthalocyanine derivative or a near-infrared-absorbing phthalocyanine pigment) may be used. In this case, it is desirable that the phthalocyanine be immobilized on a side chain of the polymer via a chemical bond so that the phthalocyanine does not enter into cells. Use of a coordinated complex, even one capable of forming a polymer, should be avoided because such a complex may release a metal ion.

The diameter of the laser beam L may be smaller than 50 μm. By connecting an optical fiber having a small core diameter to the processing nozzle 33 and then making the laser light L emitted from the laser source 31 pass through the optical fiber to the processing nozzle 33, for example, the diameter of the laser beam L discharged from the processing nozzle 33 can be made to 25 μm or smaller and accordingly the amount of energy (energy density) of the laser L per unit area can be increased. In this case, even when the maximum output of the laser source 31 is not high, a considerable amount of energy can be applied to the area irradiated with the laser L, namely the partial area where unwanted cells are present.

The shape of projection of the laser beam L applied to the to-be-irradiated layer 12 is not limited to a spot or a circle. The shape of projection of the laser beam L may be a rod-like line beam extending toward a certain direction. Using the line beam makes it possible to shorten necessary time for raster scanning a certain area in (the to-be-irradiated layer 12 of) the cell culture vessel 1.

In the embodiment above, the processing nozzle 33 configured to discharge the laser L toward the cell culture vessel 1 supported on the support 2 is mounted on the XY stage 4 and the processing nozzle 33 is moved in the X-axis direction and in the Y-axis direction. An alternative configuration may also be adopted where the support 2 supporting the cell culture vessel 1 is mounted on the displacement mechanism 4 such as the XY stage and the cell culture vessel 1 is moved in the X-axis direction and in the Y-axis direction. A yet another alternative configuration may also be adopted where one of the processing nozzle 33 and the support 2 is mounted on a linear-motor sliding platform or the like that can move in the X-axis direction and the other of these is mounted on a linear-motor sliding platform or the like that can move in the Y-axis direction, thereby the laser beam L discharged from the processing nozzle 33 being displaced in both the X-axis direction and the Y-axis direction relative to the to-be-irradiated layer 12 of the cell culture vessel 1.

The displacement mechanism 4 for displacing the target location of the laser L on the to-be-irradiated layer 12 of the cell culture vessel 1 may be a galvano scanner. As is well known, a galvano scanner is configured to turn a mirror that reflects the laser light L emitted from the laser source 31 with the use of a servo motor or a stepping motor, for example, allowing the mirror to quickly change the optical axis of the laser L. It should be noted that, in the case where a galvano scanner is used, the angle at which the optical axis of the laser light L crosses with the to-be-irradiated layer 12 of the cell culture vessel 1 cannot be maintained precisely constant. In the case where a semiconductor laser or the like is used as the laser source and the laser oscillated by the laser source is transferred to the galvano scanner through an optical fiber or the like, it is not easy to minimize the diameter of the laser beam L to be applied to the to-be-irradiated layer 12 or to minimize the scale of projection of the laser beam. For minimizing the diameter of the laser beam L or the scale of projection of the laser beam so as to enhance energy density, it is preferable to use a mechanism, such as the XY stage 4 or a linear-motor sliding platform, capable of moving the optical axis of the laser beam L in a direction parallel to the to-be-irradiated layer 12 of the cell culture vessel 1. By using a fiber laser as the laser source or converging solid-state laser light, the diameter of the laser beam L to be applied to the to-be-irradiated layer 12 or the scale of projection of the laser can be minimized.

A solid-state imaging device which is a component of the imaging device 6 for taking an image of cells in the cell culture vessel 1 may be disposed on the processing nozzle 33.

As the light source for providing light for taking an image of cells in the cell culture vessel 1, the laser light L discharged from the processing nozzle 33 may be used. In this case, the output of the laser L discharged from the processing nozzle 33 for irradiating the cell culture vessel 1 needs to be adequately lower than the output of the laser L to be applied to the cell culture vessel 1 for killing unwanted cells.

In the embodiment above, the to-be-irradiated layer 12 is formed by coating the bottom of the well 10 in the main body 11 of the cell culture vessel 1 with a polymer that is a material of the to-be-irradiated layer 12. However, it is difficult to coat the entire multidish-shape main body having a plurality of wells formed thereon with the polymer by a technique such as spin coating so as to form the to-be-irradiated layer. In view of this circumstance, an alternative configuration may also be adopted where an ingredient capable of generating heat upon irradiation with the laser light L is used to make a plate and the resulting plate is disposed on or attached to the bottom of each well in the main body to form the to-be-irradiated layer of the cell culture vessel. The plate may be made by applying a pigment capable of absorbing the laser light L to a sheet of a material, such as plastic or glass, that is transparent or light-transmissive to allow the passage of the laser light L. Alternatively, the sheet may be made with a material blend containing a pigment capable of absorbing the laser light L. Yet alternatively, the pigment-structure-containing polymer or the photoacid generator in the embodiment above may be used as the pigment capable of absorbing the laser light L.

In the embodiment above, the to-be-irradiated layer 12 is irradiated with the laser light L that is emitted from below the cell culture vessel 1 and then passes through the main body 11. An alternative configuration may also be adopted where the to-be-irradiated layer 12 is directly irradiated with the laser light L emitted from above, namely from the side of the surface of the to-be-irradiated layer 12 (without the laser light passing through the main body 11). In this case, it is not necessary for the main body 11 to be transparent or light-transmissive for allowing the passage of the laser light L. It is preferable that the focus of the laser light L for irradiation be adjusted not on cells on the to-be-irradiated layer 12 but on the to-be-irradiated layer 12.

For culturing iPS cells and other cells in the cell culture vessel 1, feeder cells may be concurrently used. The laser processing machine according to the present invention can also be used to kill feeder cells no longer required in the cell culture vessel 1.

In the case where a cell aggregate 9 which has proliferated in a cell culture vessel without the to-be-irradiated layer 12 formed is culled, cut or trimmed as described above, it is possible to focus laser light L discharged from a processing nozzle 33 of the laser processing machine to a layer of the cell aggregate 9 on the cell culture vessel and directly irradiate the cell aggregate 9 with the laser light L so as to annihilate unwanted cells to be killed. In this case, the laser L may be a pulsed laser like a picosecond laser or a femtosecond laser with a ultrashort pulse width.

The cell treatment system according to the present invention can be used for not only culturing undifferentiated iPS cells but also induction of differentiation after generating iPS cell colonies. Because, similarly to the process in culturing undifferentiated iPS cells, slow-growing cell aggregates 9 are culled, fast-growing cell aggregates 9 are cut or trimmed, and unwanted cells which are undifferentiated or differentiated into cells other than target cells are killed and eliminated, in order to obtain cell aggregates 9 each having a desired size and consisting of the target cells which are differentiated cells when a predetermined culture time elapses.

A cell aggregate 9 having an proper area or size smaller than an upper limit may be trimmed such that cells on the periphery 92 of the cell aggregate 9 are killed. It is possible for the user to arbitrarily set the width of the periphery 92 in which the cells are annihilated or the size of a trimmed cell aggregate 9 (the diameter of the circle 64). The computer 5 receives an input of the width of the periphery 92 to be cut in the trimming or the size of the cell aggregate 9 after the trimming by the user via the input device 8, stores the input value in the main memory 5b or the auxiliary memory device 5c, and uses it for determining target coordinates to be irradiated with the laser L in the trimming of the cell aggregate 9 on the cell culture vessel 1.

Regarding to the concrete configurations of the respective components, various modifications are possible without departing from the scope and spirit of the present invention.

INDUSTRIAL APPLICABILITY

The present invention is applicable to killing unwanted cells among cells cultured on a cell culture vessel and nurturing desired cell aggregates.

DESCRIPTION OF THE REFERENCE SIGNS

1: Culture vessel
3: Laser irradiator
33: Processing nozzle
4: Displacement mechanism (XY stage)
51: Analysis unit
52: Control unit
6: Imaging device
7: Display device
8: Input device
9: Cell aggregate
L: Laser light

The invention claimed is:

1. A cell treatment system to kill unwanted cells among cells cultured on a cell culture vessel and nurture desired cell aggregates, the cell treatment system comprising:
an imaging device to image all or a Part of the cell culture vessel, wherein a plurality of cell aggregates that each contain a plurality of cells exist on the cell culture vessel;
an analyzer programmed to calculate an area or size of one or each of cell aggregates existing on the cell culture vessel based on pixel values from which an image captured by the imaging device is constituted, wherein the analyzer is programmed to make a judgement on whether the area or size of each of the cell aggregates on the cell culture vessel exceeds a proper upper limit or a proper lower limit according to culture time;
a display device to show a result of the judgement about each of the cell aggregates existing on the cell culture vessel according to the culture time by the analyzer on a display;
a laser irradiator to emit laser toward the cell culture vessel so as to kill cells existing on the cell culture vessel;
an input device configured to receive an operation input by a user, the operation input designating cells to be killed with irradiation of the laser or cells to survive without the irradiation of the laser among the cells existing on the cell culture vessel, or the operation input designating a position to be irradiated with the laser or a position not to be irradiated with the laser on the cell culture vessel; and
a controller programmed to control a position irradiated with the laser emitted from the laser irradiator toward the cell culture vessel in accordance with the operation input received by the input device.

2. The cell treatment system according to claim 1, wherein the analyzer is programmed to memorize an upper limit or a lower limit on the area or size of a cell aggregate and makes a judgement on whether the area or size of each of the cell aggregates existing on the cell culture vessel exceeds the upper limit or the lower limit.

3. The cell treatment system according to claim 2, wherein the controller controls the laser irradiator such that the laser is emitted so as to kill a cell aggregate which has an area or size smaller than the lower limit among the cell aggregates existing on the cell culture vessel, and cut a cell aggregate which has an area or size larger than the upper limit or reduce the area or size of it among the cell aggregates existing on the cell culture vessel.

4. The cell treatment system according to claim 2, wherein the upper limit and the lower limit of the area or size of the cell aggregate varies depending on the culture time.

5. The cell treatment system according to claim 2, wherein a region on the cell culture vessel where a cell aggregate has an area that is within the upper limit and the lower limit according to culture time comprises a proper range according to a judgement condition.

6. The cell treatment system according to claim 5, wherein the proper range varies as cell culture time passes.

7. The cell treatment system according to claim 5, wherein the analyzer is configured to calculate that each of the cell aggregates is within the proper range based on at least one judgement condition of a plurality of judgement conditions, the judgement conditions comprising;
transmittance of the cell aggregate;
roundness of the cell aggregate;
density of cells of the cell aggregate; and
whether the cells comprise target cells or not.

8. The cell treatment system according to claim 7, wherein the roundness of a shape of each of the cell aggregates is calculated, and the analyzer judges that a cell aggregate with the roundness smaller than the lower limit device is to be killed, or to be trimmed so that the cells on a periphery of the cell aggregate are killed and the shape of the cell aggregate approaches a perfect circle.

9. The cell treatment system according to claim 7, wherein the density of cells of each of the cell aggregates is calculated, and the analyzer judges that a cell aggregate with the density smaller than the lower limit or larger than the upper limit in the cell aggregate is to be killed.

10. The cell treatment system according to claim 2, wherein
the controller controls the laser irradiator such that the laser is emitted so as to kill a cell aggregate which has the roundness exceeding the lower limit among the cell aggregates existing on the cell culture vessel, and the laser irradiator cuts the cell aggregate which has the roundness exceeding the upper limit or reduce the area or size of it among the cell aggregates existing on the cell culture vessel.

11. A cell treatment system to kill unwanted cells among cells cultured on a cell culture vessel and nurture desired cell aggregates, the cell treatment system comprising:
   an imaging device to image all or a part of the cell culture vessel, wherein a plurality of cell aggregates that each contain a plurality of cells exist on the cell culture vessel;
   an analyzer programmed to calculate an area or size of one or each of cell aggregates existing on the cell culture vessel based on pixel values from which an image captured by the imaging device is constituted, programmed to memorize an upper limit or a lower limit on the area or size of a cell aggregate according to culture time, and programed to make a judgement on whether the area or size of each of the cell aggregates existing on the cell culture vessel exceeds the upper limit or the lower limit;
   a laser irradiator to emit laser toward the cell culture vessel so as to kill cells existing on the cell culture vessel; and
   a controller programmed to control a position irradiated with the laser emitted from the laser irradiator toward the cell culture vessel in accordance with a result of the judgement by the analyzer.

12. The cell treatment system according to claim 11, wherein the controller controls the laser irradiator such that the laser is emitted so as to kill a cell aggregate which has an area or size smaller than the lower limit among the cell aggregates existing on the cell culture vessel, and cut a cell aggregate which has an area or size larger than the upper limit or reduce the area or size of it among the cell aggregates existing on the cell culture vessel.

13. The cell treatment system according to claim 11, wherein
   the controller performs the laser irradiation on a region in the cell culture vessel where a cell aggregate having an area or size that exceeds the upper limit or the lower limit exists.

14. The cell treatment system according to claim 11, wherein
   the controller performs the laser irradiation on a region in the cell culture vessel where a cell aggregate having an area that exceeds the upper limit or the lower limit exists.

15. The cell treatment system according to claim 11, wherein
   the controller performs the laser irradiation on a region in the cell culture vessel where a cell aggregate having a size that exceeds the upper limit or the lower limit exists.

16. The cell treatment system according to claim 11, wherein
   the upper limit and the lower limit of the area or size of the cell aggregate varies depending on the culture time.

17. The cell treatment system according to claim 11, wherein
   a region on the cell culture vessel where a cell aggregate has an area that is within the upper limit and the lower limit according to culture time comprises a proper range according to a judgement condition.

18. The cell treatment system according to claim 17, wherein
   the analyzer is configured to calculate that each of the cell aggregates is within the proper range based on at least one judgement condition of a plurality of judgement conditions, the judgement conditions comprising;
   transmittance of the cell aggregate;
   roundness of the cell aggregate;
   density of cells of the cell aggregate; and
   whether the cells comprise target cells or not.

19. The cell treatment system according to claim 18, wherein
   the roundness of a shape of each of the cell aggregates is calculated, and the analyzer judges that a cell aggregate with the roundness smaller than the lower limit device is to be killed, or to be trimmed so that the cells on the periphery of the cell aggregate are killed and the shape of the cell aggregate approaches a perfect circle.

20. A cell treatment system to kill unwanted cells among cells cultured on a cell culture vessel and nurture desired cell aggregates, the cell treatment system comprising:
   an imaging device to image all or a part of the cell culture vessel, wherein a plurality of cell aggregates that each contain a plurality of cells exist on the cell culture vessel;
   an analyzer programmed to calculate a feature amount of one or each of cell aggregates existing on the cell culture vessel based on pixel values from which an image captured by the imaging device is constituted, wherein the analyzer is programmed to make a judgement on whether the feature amount of each of the cell aggregates on the cell culture vessel exceeds a proper upper limit or a proper lower limit according to culture time, wherein, at least one of:
      a cell aggregate with a feature amount smaller than the lower limit of the proper range is a bad aggregate in which the cells have not successfully proliferated and which have not grown in accordance with the culture time, or,
      a cell aggregate with a feature amount larger than the upper limit of the proper range grows excessively fast beyond supposition, although the cells proliferates themselves;
   a display device to show a result of the judgement about the feature amount of each of the cell aggregates existing on the cell culture vessel according to the culture time by the analyzer on a display;
   a laser irradiator to emit laser toward the cell culture vessel so as to kill cells existing on the cell culture vessel;
   an input device configured to receive an operation input by a user, the operation input designating cells to be killed with irradiation of the laser or cells to survive without the irradiation of the laser among the cells existing on the cell culture vessel, or the operation input designating a position to be irradiated with the laser or a position not to be irradiated with the laser on the cell culture vessel; and
   a controller programmed to control a position irradiated with the laser emitted from the laser irradiator toward the cell culture vessel in accordance with the operation input received by the input device.

* * * * *